United States Patent

Santel et al.

[11] Patent Number: 5,990,044
[45] Date of Patent: Nov. 23, 1999

[54] SELECTIVE HERBICIDES BASED ON ARYL URACILS

[75] Inventors: Hans-Joachim Santel; Markus Dollinger, both of Leverkusen; Roland Andree; Mark Wilhelm Drewes, both of Langenfeld, all of Germany

[73] Assignee: Bayer Aktiengesellschaft, Leverkusen, Germany

[21] Appl. No.: 09/050,278

[22] Filed: Mar. 30, 1998

Related U.S. Application Data

[63] Continuation of application No. 08/793,396, filed as application No. PCT/EP95/03313, Aug. 21, 1995, abandoned.

[30] Foreign Application Priority Data

Sep. 2, 1994 [DE] Germany ............... 44 31 219

[51] Int. Cl.$^6$ ............... A01N 43/50; A01N 43/653; A01N 47/28; A01N 57/02
[52] U.S. Cl. ............... 504/128; 504/132; 504/134; 504/136
[58] Field of Search ............... 504/128, 132, 504/134, 136

[56] References Cited

U.S. PATENT DOCUMENTS 5,084,084 1/1992 Santow et al. ............... 71/92
5,567,670 10/1996 Amuit et al. ............... 504/230

FOREIGN PATENT DOCUMENTS 4 412 079 2/1995 Germany.
WO 93/14073 7/1993 WIPO.

OTHER PUBLICATIONS

Chemical Abstract of JP–A–06 271 409 (Sep. 27,), Week 9443 AN–347010.

Chemical Abstract of JP–A–07 053 313 (Feb. 28, 1995), Week 9517 AN 95–128198.

R. Wegler Chemie der Pfanzenschutz–und Schädlingsbekämpfungsmittel. Band 2.' 1970, see p. 354, last paragraph, and p. 356, line 8–line 18.

*Primary Examiner*—S. Mark Clardy
*Attorney, Agent, or Firm*—Sprung Kramer Schaefer & Briscoe

[57] ABSTRACT

The invention relates to new herbicidal synergistic active compound combinations which are composed of, on the one hand, known aryluracils (or aryl-thiouracils—or compounds which are isomeric to these aryluracils or aryl-thiouracils) and, on the other hand, further known herbicides belonging to other substance classes and which can be used particularly successfully for selective weed control in a variety of crops, in particular in maize.

8 Claims, No Drawings

SELECTIVE HERBICIDES BASED ON ARYL URACILS

This is a continuation application of application Ser. No. 08/793,396, filed on Feb. 24, 1997, now abandoned, which was filed under 35 USC 371 on the national stage of international application PCT/EP95/03313, filed Aug. 21, 1995.

The invention relates to new herbicidal, synergistic combinations of active compounds composed, on the one hand, of known aryluracils (or aryl-thiouracils - or compounds which are isomeric to these aryluracils or aryl-thiouracils) and, on the other hand, of further known herbicides belonging to different classes of substances, and which can be used especially successfully for selective weed control in a variety of crops, in particular in maize.

Aryluracils (or aryl-thio-uracils), being herbicides with a broad range of action, are the subject-matter of a series of patent applications (cf. WO-A 91/00278, U.S. Pat. No. 4,979,982, U.S. Pat. No. 5,169,430, EP-A 408382, EP-A 563384, U.S. Pat. No. 5,084,084, U.S. Pat. No. 5,127,935, U.S. Pat. No. 5,154,755, German Patent Specification 4327743, German Patent Specification 4343451, German Patent Specification 4414326. However, the activity of the known aryluracils (or aryl-(thio)uracils) displays a series of gaps, in particular relative to monocotyledon weeds.

Surprisingly, it has now been found that a series of known herbicidally active compounds from the group of the aryluracils (or arylthiouracils—or compounds which are isomeric to these aryluracils or aryl-thiouracils) show pronounced synergistic effects regarding the herbicidal activity when used jointly with known herbicidally active compounds, for example from the substance classes of the alkylanilines, carboxylic acids, carboxamides, diazin(on)es or triazin(on)es, ureas, nitriles, thiocarbamates and triazolinones, and can be used especially advantageously as effective broad-range combination products for the selective control of both monocotyledon and dicotyledon weeds pre- and post-emergence in monocotyledon crops such as, for example, maize.

The invention relates to synergistic herbicidal compositions, characterized in that they comprise an effective amount of an active compound combination composed of (1) an aryluracil, or an aryl-thiouracil, of the general formula (I)

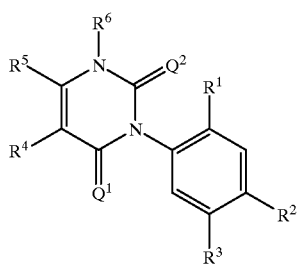

or a compound of the general formula (Ia) which is isomeric hereto

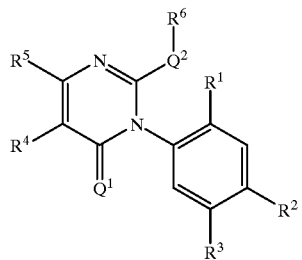

where, in formulae (I) and (Ia), in each case
 $Q^1$ represents oxygen or sulphur,
 $Q^2$ represents oxygen or sulphur,
 $R^1$ represents hydrogen or halogen,
 $R^2$ represents halogen or cyano,
 $R^3$ represents the group below $-A^1-A^2-A^3$ in which
 $A^1$ represents a single bond, or represents oxygen, sulphur, —SO—, —SO$_2$—, —CO— or the group —N-A$^4$- where $A^4$ represents hydrogen, hydroxyl, alkyl, alkoxy, aryl, alkylsulphonyl or arylsulphonyl, or ($A^1$) represents in each case optionally substituted alkanediyl, alkenediyl, azaalkenediyl, alkinediyl, cycloalkanediyl, cycloalkenediyl or arenediyl,
 $A^2$ represents a single bond, or represents oxygen, sulphur, —SO—, —SO$_2$—, —CO— or the group —N-A$^4$- where $A^4$ represents hydrogen, alkyl, aryl, alkylcarbonyl, alkylsulphonyl or arylsulphonyl, or ($A^2$) represents in each case optionally substituted alkanediyl, alkenediyl, azaalkenediyl, alkinediyl, cycloalkanediyl, cycloalkenediyl or arenediyl, and
 $A^3$ represents hydrogen, hydroxyl, mercapto, amino, cyano, isocyano, thiocyanato, nitro, carboxyl, carbamoyl, thiocarbamoyl, sulpho, chlorosulphonyl, halogen, or represents in each case optionally substituted alkyl, alkoxy, alkylthio, alkylsulphinyl, alkylsulphonyl, alkylamino, dialkylamino, alkoxycarbonyl, dialkoxy(thio)phosphoryl, alkenyl, alkenyloxy, alkenylamino, alkylideneamino, alkenyloxycarbonyl, alkinyl, alkinyloxy, alkinylamino, alkinyloxycarbonyl, cycloalkyl, cycloalkyloxy, cycloalkylalkyl, cycloalkylalkoxy, cycloalkylideneamino, cycloalkyloxycarbonyl, cycloalkylalkoxycarbonyl, aryl, aryloxy, arylalkyl, arylalkoxy, aryloxycarbonyl, arylalkoxycarbonyl, heterocyclyl, heterocyclylalkyl, heterocyclylalkoxy or heterocyclylalkoxycarbonyl,
 $R^4$ represents hydrogen, halogen or optionally substituted alkyl,
 $R^5$ represents hydrogen, halogen or optionally substituted alkyl, and
 $R^6$ represents hydrogen, hydroxyl, amino, or represents in each case optionally substituted alkyl, alkoxy, alkenyl or alkinyl, ("active compounds of group 1") and (2) a herbicidal active compound from a second group of herbicides ("active compounds of group 2"), which contains the compound classes (a) to (j) given below:

(a) heteroaryloxyacetamides of the general formula (II)

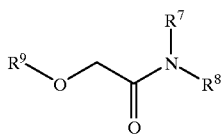

(II)

in which
R[7] represents in each case optionally substituted alkyl, alkenyl, alkinyl or alkoxy,
R[8] represents in each case optionally substituted alkyl, alkenyl, alkinyl or phenyl, and
R[9] represents optionally substituted heteroaryl;
(b) carbamoyltriazolinones of the general formula (III)

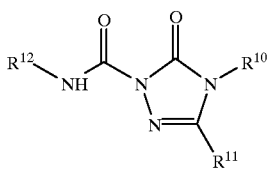

(III)

in which
R[10] represents hydrogen, hydroxyl, amino, or represents in each case optionally substituted alkyl, alkenyl, alkinyl, alkoxy, alkenyloxy, alkinyloxy, alkylamino, alkenylamino, alkinylamino, alkylideneamino, dialkylamino, cycloalkyl, cycloalkylalkyl, aryl or arylalkyl,
R[11] represents in each case optionally substituted alkyl, alkenyl, alkinyl, alkoxy, alkenyloxy, alkinyloxy, alkylthio, alkenylthio, alkinylthio, alkylamino, alkenylamino, alkinylamino, dialkylamino, cycloalkyl, cycloalkyloxy, cycloalkylalkyl, aryl, aryloxy, arylthio, arylamino or arylalkyl, and
R[12] represents in each case optionally substituted alkyl, alkenyl, alkinyl, cycloalkyl, cycloalkylalkyl, arylalkyl, arylalkenyl or arylalkinyl;
(c) alkylanilines such as, for example, N-(1-ethyl-propyl)-3,4-dimethyl-2,6-dinitro-aniline (pendimethalin) or N,N-dipropyl-2,6-dinitro-4-trifluoro-methyl-aniline (trifluralin);
(d) carboxylic acids such as, for example, 3,6-dichloro-pyridine-2-carboxylic acid (clopyralid), 2,4-dichlorophenoxy acetic acid (2,4-D), 3,6-dichloro-2-methoxy-benzoic acid (dicamba), 4-amino-3,5-dichloro-6-fluoro-pyridin-2-yl-oxy-acetic acid (fluroxypyr), ammonium 2-amino-4-(hydroxymethylphosphinyl)-butanoate (glufosinate-ammonium), N-phosphonomethyl-glycine (glyphosate), 2-(4,5-dihydro-4-methyl-4-i-propyl-5-oxo-1H-imidazol-2-yl)-5-ethyl-pyridine-3-carboxylic acid (imazethapyr) or 2-(4,5-dihydro-4-methyl-4-i-propyl-5-oxo-1H-imidazol-2-yl)-quinoline-3-carboxylic acid (imazaquin);
(e) carboxamides, such as, for example, N-(2-methoxy-1-methyl-ethyl)-N-(2-ethyl-6-methyl-phenyl)-2-chloro-acetamide (metolachlor), N-ethoxymethyl-N-(2-ethyl-6-methyl-phenyl)-2-chloro-acetamide (acetochlor), N-methoxymethyl-N-(2,6-dimethyl-phenyl)-2-chloro-acetamide (alachlor), N-(2-methoxy-1-methyl-ethyl)-N-(2,4-dimethyl-3-thienyl)-2-chloro-acetamide (dimethanamid), N-(1H-pyrazol-1-yl-methyl)-N-(2,6-dimethyl-phenyl)-2-chloroacetamide (metazachlor) or N-i-propyl-N-phenyl-2-chloro-acetamide (propachlor);

(f) diazin(on)es, or triazin(on)es, such as, for example, 2-chloro-4-ethylamino-6-i-propylamino-1,3,5-triazine (atrazine), 3-i-propyl-1H-2,1,3-benzothiadiazin-4(3H)-one 2,2-dioxide (bentazone), 2-chloro-4-ethylamino-6-(1-cyano-1-methyl-ethylamino)-1,3,5-triazine(cyanazine), 4-amino-6-t-butyl-4,5-dihydro-3-methylthio-1,2,4-triazin-5-one (metribuzin), O-(6-chloro-3-phenyl-4-pyridazinyl) S-octyl thiocarbonate (pyridate); 2-chloro-4,6-bis-ethylamino-1,3,5-triazine (simazine) or 2-chloro-4-ethylamino-6-t-butylamino-1,3,5-triazine (terbuthylazine);
(g) ureas, such as, for example, N-(4,6-dimethoxy-pyrimidin-2-yl)-N'-(3-chloro-4-methoxycarbonyl-1-methyl-pyrazol-5-yl-sulphonyl)-urea (clopyrasulfurone), N-methoxy-N-methyl-N'-[4-(3,4-dihydro-2-methoxy-2,4,4-trimethyl-2H-1-benzopyran 7-yl-oxy)-phenyl]-urea (metobenzuron), N-(4,6-dimethoxy-pyrimidin-2-yl)-N'-(3-dimethylaminocarbonyl-pyridin-2-yl-sulphonyl)-urea (nicosulfuron),N-(4,6-bis-difluoromethoxy-pyrimidin-2-yl)-N'-(2-methoxycarbonyl-phenylsulphonyl)-urea (primisulfuron-methyl),N-(4-methoxy-6-methyl-1,3,5-triazin-2-yl)-N'-[2-(3,3,3-trifluoro-propyl)-phenylsulphonyl]-urea (prosulfuron), N-(4,6-dimethoxy-pyrimidin-2-yl)-N'-(3-ethylsulphonyl-pyridin-2-yl-sulphonyl)-urea (rimsulfuron) or N-(4-methoxy-6-methyl-1,3,5-triazin-2-yl)-N'-(2-methoxycarbonyl-3-thienyl-sulphonyl)urea (thifensulfuron-methyl);
(h) nitriles such as, for example, 3,5-dibromo-4-hydroxy-benzonitrile (bromoxynil) or 3,5-diiod-4-hydroxy-benzonitrile (ioxynil);
(i) thiocarbamates such as, for example, S-ethyl di-i-butylthiocarbamate (butylate) or S-ethyl dipropylthiocarbamate (EPTC);
(j) active compounds from a variety of substance groups such as, for example, N-2,6-difluoro-phenyl-5-methyl-[1,2,4]-triazolo-[1,5-a]-pyrimidine-2-sulphonamide (flumetsulam), 1,1'-dimethyl-4,4'-bipyridinium chloride (paraquat) or 2-(2-chloro4-methylsulphonyl-benzoyl)-1,3-cyclohexanedione (sulcotrione),
In each case 0.001 to 1000 parts by weight of active compound of group 2 generally being used per part by weight of active compound of the group 1.

Herbicidal compositions according to the invention which are of particular interest are those with
(1) a compound of the formula (I) or (Ia) in which
$Q^1$ represents oxygen or sulphur,
$Q^2$ represents oxygen or sulphur,
$R^1$ represents hydrogen, fluorine, chlorine or bromine,
$R^2$ represents fluorine, chlorine, bromine, iodine or cyano,
$R^3$ represents the group below,

-A¹-A²-A³ in which
$A^1$ represents a single bond, or represents oxygen, sulphur, —SO—, —SO$_2$—, —CO— or the group —N-A⁴- in which A⁴- is hydrogen, hydroxyl, $C_1$–$C_4$-alkyl, $C_1$–$C_4$-alkoxy, phenyl, $C_1$–$C_4$-alkylsulphonyl or phenylsulphonyl, or (A¹) represents $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene, each of which is optionally substituted by fluorine, chlorine or bromine,
$A^2$ represents a single bond, or represents oxygen, sulphur, —SO—, —SO$_2$—, —CO— or the group —N-A⁴- in which A⁴ is hydrogen, hydroxyl, $C_1$–$C_4$- alkyl, $C_1$–$C_4$-alkoxy, phenyl, $C_1$–$C_4$-alkylsulphonyl or phenylsulphonyl, or ($A^2$) represents $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene, each of which is optionally substituted by fluorine, chlorine or bromine, $A^3$ represents hydrogen, hydroxyl, amino, cyano, isocyano, thiocyanato, nitro, carboxyl, carbamoyl, thiocarbamoyl, sulpho, chlorosulphonyl, halogen, or represents alkyl, alkoxy, alkylthio, alkylsulphinyl, alkylsulphonyl, alkylamino, dialkylamino, alkoxycarbonyl or dialkoxy(thio)phosphoryl, each of which has 1 to 6 carbon atoms in the alkyl groups and each of which is optionally substituted by halogen or $C_1$–$C_4$-alkoxy, or represents alkenyl, alkenyloxy, alkenylamino, alkylideneamino, alkenyloxycarbonyl, alkinyl, alkinyloxy, alkinylamino or alkinyloxycarbonyl, each of which has 2 to 6 carbon atoms in the alkenyl, alkylidene or alkinyl groups and each of which is optionally substituted by halogen, or represents cycloalkyl, cycloalkyloxy, cycloalkylalkyl, cycloalkylalkoxy, cycloalkylideneamino, cycloalkyloxycarbonyl or cycloalkylalkoxycarbonyl, each of which has 3 to 6 carbon atoms in the cycloalkyl groups and, if appropriate, 1 to 4 carbon atoms in the alkyl groups and each of which is optionally substituted by halogen, cyano, carboxyl, $C_1$–$C_4$-alkyl and/or $C_1$–$C_4$-alkoxy-carbonyl, or represents phenyl, phenyloxy, phenyl-$C_1$–$C_4$-alkyl, phenyl-$C_1$–$C_4$-alkoxy, phenyloxycarbonyl or phenyl-$C_1$–$C_4$-alkoxycarbonyl, each of which is optionally substituted by nitro, cyano, carboxyl, halogen $C_1$–$C_4$-alkyl, $C_1$–$C_4$-halogenoalkyl, $C_1$–$C_4$-alkyloxy, $C_1$–$C_4$-halogenoalkyloxy and/or $C_1$–$C_4$-alkoxy-carbonyl, or (in each case optionally fully or partially hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolyl-$C_1$–$C_4$-alkyl, furyl-$C_1$–$C_4$-alkyl, thienyl-$C_1$–$C_4$-alkyl, oxazolyl-$C_1$–$C_4$-alkyl, isoxazol-$C_1$–$C_4$-alkyl, thiazol-$C_1$–$C_4$-alkyl, pyridinyl-$C_1$–$C_4$-alkyl, pyrimidinyl-$C_1$–$C_4$-alkyl, pyrazolylmethoxy, furylmethoxy, or perhydropyranylmethoxy or pyridylmethoxy, $R^4$ represents hydrogen, fluorine, chlorine, bromine, or alkyl having 1 to 4 carbon atoms which is optionally substituted by fluorine and/or chlorine, $R^5$ represents hydrogen, fluorine, chlorine, bromine, or alkyl having 1 to 4 carbon atoms which is optionally substituted by fluorine and/or chlorine, and $R^6$ represents hydrogen, hydroxyl, amino, or represents alkyl, alkoxy, alkenyl or alkinyl, each of which has up to 4 carbon atoms and each of which is optionally substituted by fluorine, chlorine or cyano, and (2) an active compound from a second group of herbicides which contains the compound classes (a) to (j) given below:

(a) heteroaryloxyacetamides of the formula (II) in which $R^7$ represents alkyl, alkenyl, alkinyl or alkoxy, each of which has up to 6 carbon atoms and each of which is optionally substituted by halogen, cyano or $C_1$–$C_4$-alkoxy, $R^8$ represents alkyl, alkenyl or alkinyl, each of which has up to 6 carbon atoms and each of which is optionally substituted by halogen, cyano or $C_1$–$C_4$-alkoxy, or represents phenyl which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy, and $R^9$ represents heteroaryl from the series consisting of 1,3-thiazol-2-yl, 1,2,4-thiadiazol-5-yl, 1,3,4-thiadiazol-2-yl, benzoxazol-2-yl, benzthiazol-2-yl, each of which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy;

(b) carbamoyltriazolinones of the formula (III) in which $R^{10}$ represents hydrogen, hydroxyl, amino, or represents alkyl, alkenyl, alkinyl, alkoxy, alkenyloxy, alkinyloxy, alkylamino, alkenylamino, alkinylamino, alkylideneamino or dialkylamino, each of which has up to 6 carbon atoms and each of which is optionally substituted by halogen or cyano, or represents cycloalkyl, cycloalkylalkyl, each of which has 3 to 6 carbon atoms in the cycloalkyl groups and, if appropriate, 1 to 4 carbon atoms in the alkyl group and each of which is optionally substituted by halogen, cyano or $C_1$–$C_4$-alkyl, or represents phenyl or phenyl-$C_1$–$C_4$-alkyl, each of which is optionally substituted by halogen, cyano, $C_1$–$C_4$-alkyl or $C_1$–$C_4$-alkoxy, $R^{11}$ represents alkyl, alkenyl, alkinyl, alkoxy, alkenyloxy, alkinyloxy, alkylthio, alkenylthio, alkinylthio, alkylamino, alkenylamino, alkinylamino or dialkylamino, each of which has up to 6 carbon atoms and each of which is optionally substituted by halogen, cyano, $C_1$–$C_4$-alkoxy or $C_1$–$C_4$-alkylthio, or represents cycloalkyl, cycloalkyloxy or cycloalkylalkyl, each of which has 3 to 6 carbon atoms in the cycloalkyl groups and, if appropriate, 1 to 4 carbon atoms in the alkyl group and each of which is optionally substituted by halogen, cyano or $C_1$–$C_4$-alkyl, or represents phenyl, phenoxy, phenylthio, phenylamino or phenyl-$C_1$–$C_4$-alkyl, each of which is optionally substituted by halogen, cyano, $C_1$–$C_4$-alkyl or $C_1$–$C_4$-alkoxy, and $R^{12}$ represents alkyl, alkenyl, alkinyl, each of which has up to 10 carbon atoms and each of which is optionally substituted by halogen, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkylamino or di-($C_1$–$C_4$-alkyl)-amino, or represents cycloalkyl or cycloalkylalkyl, each of which has 3 to 6 carbon atoms in the cycloalkyl moiety and, if appropriate, I to 4 carbon atoms in the alkyl moiety and each of which is optionally substituted by halogen, cyano or $C_1$–$C_4$-alkyl, or represents phenyl-$C_1$–$C_6$-alkyl, phenyl-$C_2$–$C_6$-alkenyl or phenyl-$C_2$–$C_6$-alkinyl, each of which is optionally substituted by halogen, cyano, $C_1$–$C_4$-alkyl or $C_1$–$C_4$-alkoxy;

(c) alkylanilines such as, for example, N-(1-ethyl-propyl)-3,4-dimethyl-2,6-dinitro-aniline (pendimethalin) or N,N-dipropyl-2,6-dinitro-4-trifluoromethyl-aniline (trifluralin);

(d) carboxylic acids such as, for example, 3,6-dichloro-pyridine-2-carboxylic acid (clopyralid), 2,4-dichloro-phenoxy acetic acid (2,4-D), 3,6-dichloro-2-methoxy-benzoic acid (dicamba), 4-amino-3,5-dichloro-6-fluoro-pyridin-2-yl-oxy-acetic acid (fluroxypyr), ammonium 2-amino-4-(hydroxymethylphosphinyl)-butanoate (glufosinate-ammonium), N-phosphonomethyl-glycine (glyphosate), 2-(4,5-dihydro-4-methyl-4-i-propyl-5-oxo-1H-imidazol-2-yl)-5-ethyl-pyridine-3-carboxylic acid (imazethapyr) or2-(4,5-dihydro-4-methyl-4-i-propyl-5-oxo-1H-imidazol-2-yl)-quinoline-3-carboxylic acid (imazaquin);

(e) carboxamides, such as, for example, N-(2-methoxy-1-methyl-ethyl)-N-(2-ethyl-6-methyl-phenyl)-2-chloro-acetamide (metolachlor), N-ethoxymethyl-N-(2-ethyl-6-methyl-phenyl)-2-chloro-acetamide (acetochlor), N-methoxymethyl-N-(2,6-dimethyl-phenyl)-2-chloroacetamide (alachlor), N-(2-methoxy-1-methyl-ethyl)-N-(2, 4-dimethyl-3-thienyl)-2-chloroacetamide (dimethanamid), N-(1H-pyrazol-1-yl-methyl)-N-(2,6-dimethylphenyl)-2-chloro-acetamide (metazachlor) or N-i-propyl-N-phenyl-2-chloro-acetamide (propachlor);

(f) diazin(on)es, or triazin(on)es, such as, for example, 2-chloro-4-ethylamino-6-i-propylamino-1,3,5-triazine (atrazine), 3-i-propyl-1H-2, 1,3-benzothiadiazin-4(3H)-one 2,2-dioxide (bentazone), 2-chloro-4-ethylamino-6-(1-cyano-1-methyl-ethylamino)-1,3,5-triazine (cyanazine), 4-amino-6-t-butyl-4,5-dihydro-3-methylthio-1,2,4-triazin-5-one (metribuzin), O-(6-chloro-3-phenyl-4-pyridazinyl) S-octyl thiocarbonate (pyridate); 2-chloro-4,6-bis-ethylamino-1,3,5-triazine (simazine) or 2-chloro4-ethylamino-6-t-butylamino-1,3,5-triazine (terbuthylazine);

(g) ureas, such as, for example, N-(4,6-dimethoxy-pyrimidin-2-yl)-N'-(3-chloro-4-methoxycarbonyl-1-methyl-pyrazol-5-yl-sulphonyl)-urea (clopyrasulfurone), N-methoxy-N-methyl-N'-[4-(3,4-dihydro-2-methoxy-2,4,4-trimethyl-2H-1-benzopyran7-yl-oxy)-phenyl]-urea (metobenzuron), N-(4,6-dimethoxy-pyrimidin-2-yl)-N'-(3-dimethylaminocarbonyl-pyridin-2-yl-sulphonyl)-urea (nicosulfuron), N-(4,6-bis-difluoromethoxypyrimidin-2-yl)-N'-(2-methoxycarbonyl-phenylsulphonyl)-urea (primisulfuron-methyl),N-(4-methoxy-6-methyl-1,3,5-triazin-2-yl)-N'-[2-(3,3,3-trifluoro-propyl)-phenylsulphonyl]-urea (prosulfuron), N-(4,6-dimethoxypyrimidin-2-yl)-N'-(3-ethylsulphonyl-pyridin-2-yl-sulphonyl)-urea (rimsulfuron) or N-(4-methoxy-6-methyl-1,3,5-triazin-2-yl)-N'-(2-methoxycarbonyl-3-thienyl-sulphonyl)-urea (thifensulfuron-methyl);

(h) nitriles such as, for example, 3,5-dibromo4-hydroxy-benzonitrile (bromoxynil) or 3,5-diiod4-hydroxy-benzonitrile (ioxynil);

(i) thiocarbamates such as, for example, S-ethyl di-i-butylthiocarbamate (butylate) or S-ethyl dipropylthiocarbamate (EPTC);

(j) active compounds from a variety of substance groups such as, for example, N-2,6-difluoro-phenyl-5-methyl-[1,2,4]-triazolo- [1,5-a]-pyrimidine-2-sulphonamide (flumetsulam), 1,1'-dimethyl-4,4'-bipyridinium chloride (paraquat) or 2-(2-chloro-4-methylsulphonylbenzoyl)-1,3-cyclohexanedione (sulcotrione), in each case 0.01 to 100 parts by weight of active compound of group 2 preferably being used per part by weight of active compound of the group 1.

Herbicidal compositions according to the invention which are of very particular interest are those with (1) a compound of the formula (I) or (Ia) in which $Q^1$ represents oxygen or sulphur, $Q^2$ represents oxygen or sulphur, $R^1$ represents hydrogen, fluorine, chlorine or bromine, $R^2$ represents fluorine, chlorine, bromine, iodine or cyano, $R^3$ represents the group below,

-$A^1$-$A^2$-$A^3$ in which $A^1$ represents a single bond, or represents oxygen, sulphur, —SO—, —SO$_2$—, —CO— or the group —N-$A^4$- where $A^4$ represents hydrogen, hydroxyl, methyl, ethyl, n- or i-propyl, methoxy, ethoxy, n- or i-propoxy, methylsulphonyl or ethylsulphonyl, or ($A^1$) represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl, propine-1,2-diyl or propine-1,3-diyl, $A^2$ represents a single bond, or represents oxygen, sulphur, —SO—, —SO, —CO— or the group —N-$A^4$- where $A^4$ represents hydrogen, hydroxyl, methyl, ethyl, n- or i-propyl, methoxy, ethoxy, n- or i-propoxy, methylsulphonyl, ethylsulphonyl, n- or i-propylsulphonyl or phenylsulphonyl, or ($A^2$) represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl, propine-1,2-diyl or propine-1,3-diyl, $A^3$ represents hydrogen, hydroxyl, amino, cyano, nitro, carboxyl, carbamoyl, sulpho, fluorine, chlorine, bromine, or represents in each case optionally fluorine-, chlorine-, methoxy- or ethoxy-substituted methyl, ethyl, n- or i-propyl, n-, i-, s- or t-butyl, n-, i-, s- or t-pentyl, methoxy, ethoxy, n- or i-propoxy, n-, i-, s- or t-butoxy, n-, i-, s- or t-pentyloxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, methoxycarbonyl, ethoxycarbonyl, n- or i-propoxycarbonyl, dimethoxyphosphoryl, diethoxyphosphoryl, dipropoxyphosphoryl or diisopropoxyphosphoryl, or represents. propenyl, butenyl, propenyloxy, butenyloxy, propenylamino, butenylamino, propylideneamino, butylideneamino, propenyloxycarbonyl, butenyloxycarbonyl, propinyl, butinyl, propinyloxy, butinyloxy, propinylamino, butinylamino, propinyloxycarbonyl or butinyloxycarbonyl, each of which is optionally substituted by fluorine or chlorine, or represents cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopentylideneamino, cyclohexylideneamino, cyclopentyloxycarbonyl, cyclohexyloxycarbonyl, cyclopentylmethoxycarbonyl or cyclohexylmethoxycarbonyl, each of which is optionally substituted by fluorine, chlorine, cyano, carboxyl, methyl, ethyl, n- or i-propyl, methoxycarbonyl or ethoxycarbonyl, or represents in each case optionally nitro-, cyano-, carboxyl-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methoxycarbonyl- and/or ethoxycarbonyl- substituted phenyl, phenyloxy, benzyl, phenylethyl, benzyloxy, phenyloxycarbonyl, benzyloxycarbonyl, (in each case optionally fully or partially hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl, thienylmethyl, oxazolylmethyl, isoxazolmethyl, thiazolmethyl, pyridinylmethyl, pyrimidinylmethyl, pyrazolylmethoxy, furylmethoxy or pyridylmethoxy, $R^4$ represents hydrogen, fluorine, chlorine, or represents methyl or ethyl, each of which is optionally substituted by fluorine and/or chlorine, $R^5$ represents hydrogen, fluorine, chlorine, or represents methyl or ethyl, each of which is optionally substituted by fluorine and/or chlorine, and $R^6$ represents hydrogen, hydroxyl, amino, or represents methyl, ethyl, n- or i-propyl, methoxy, ethoxy, n- or i-propoxy, propenyl or propinyl, each of which is optionally substituted by fluorine, chlorine or cyano, and (2) an active compound from a second group of herbicides which contains the compound classes (a) to (j) given below:

(a) heteroaryloxyacetamides of the formula (II) in which $R^7$ represents methyl, ethyl, n- or i-propyl, n-, i- or s-butyl, propenyl, butenyl, propinyl, butinyl, methoxy, ethoxy, n- or i-propoxy, n-, i-, s- or t-butoxy, each of which is optionally substituted by fluorine, chlorine, cyano, methoxy or ethoxy, $R^8$ represents methyl, ethyl, n- or i-propyl, n-, i-, s- or t-butyl, n-, i-, s- or t-pentyl, propenyl, butenyl, propinyl or butinyl, each of which is optionally substituted by fluorine, chlorine, cyano, methoxy or ethoxy, or represents phenyl which is optionally substituted by fluorine, chlorine, bromine, cyano, methyl, ethyl, trifluoromethyl, methoxy, ethoxy, difluoromethoxy or trifluoromethoxy, and $R^9$ represents heteroaryl from the series consisting of 1,3-thiazol-2-yl, 1,2,4-thiadiazol-5-yl, 1,3,4-thiadiazol-2-yl, benzoxazol-2-yl, benzthiazol-2-yl, each of which is optionally substituted by fluorine, chlorine, bromine, cyano, methyl, ethyl, n- or i-propyl, n-, i-, s- or t-butyl, difluoromethyl, trifluoromethyl, dichloromethyl, trichloromethyl, methoxy, ethoxy, n- or i-propoxy, n-, i-, s- or t-butoxy, difluoromethoxy or trifluoromethoxy;

(b) carbamoyltriazolinones of the formula (III) in which $R^{10}$ represents hydrogen, hydroxyl, amino, or represents methyl, ethyl, n- or i-propyl, n-, i-, s- or t-butyl, propenyl, butenyl, propinyl or butinyl, methoxy, ethoxy, n- or i-propoxy, n-, i-, s- or t-butoxy, propenyloxy, butenyloxy, propinyloxy or butinyloxy, methylamino, ethylamino, n- or i-propylamino, n-, i-, s- or t-butylamino, propenylamino, butenylamino, propinylamino or butinylamino, ethylideneamino, propylideneamino, butylideneamino, dimethylamino or diethylamino, each of which is optionally substituted by fluorine, chlorine or cyano, or represents cyclopropyl, cyclobutyl, cyclopentyl, cyclohexyl, cyclopropylmethyl, cyclobutylmethyl, cyclopentylmethyl or cyclohexylmethyl, each of which is optionally substituted by fluorine, chlorine, bromine, cyano, methyl, ethyl, n- or i-propyl, or represents phenyl or benzyl, each of which is optionally substituted by fluorine, chlorine, bromine, cyano, methyl, ethyl, n- or i-propyl, n-, i-, s- or t-butyl, methoxy or ethoxy, $R^{11}$ represents methyl, ethyl, n- or i-propyl, n-, i-, s- or t-butyl, propenyl, butenyl, propinyl, butinyl, methoxy, ethoxy, n- or i-propoxy, n-, i-, s- or t-butoxy, propenyloxy, butenyloxy, propinyloxy, butinyloxy, methylthio, ethylthio, n- or i-propylthio, n-, i-, s- or t-butylthio, propenylthio, butenylthio, propinylthio, butinylthio, methylamino, ethylamino, n- or i-propylamino, n-, i-, s- or t-butylamino, propenylamino, butenylamino, propinylamino, butinylamino, dimethylamino or diethylamino, each-of which is optionally substituted by fluorine, chlorine, cyano, methoxy, ethoxy, n- or i-propoxy, methylthio, ethylthio, n- or i-propylthio, or represents cyclopropyl, cyclobutyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl or cyclohexylmethyl, each of which is optionally substituted by fluorine, chlorine, bromine, cyano, methyl, ethyl, n- or i-propyl, or represents phenyl, phenoxy, phenylthio, phenylamino or benzyl, each of which is optionally substituted by fluorine, chlorine, bromine, cyano, methyl, ethyl, n- or i-propyl, n-, i-, s- or t-butyl, methoxy or ethoxy, and $R^{12}$ represents methyl, ethyl, n- or i-propyl, n-, i-, s- or t-butyl, propenyl, butenyl, pentenyl, hexenyl, propinyl, butinyl, pentinyl or hexinyl, each of which is optionally substituted by fluorine, cyano, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, methylamino, ethylamino, n- or i-propylamino, n-, i-, s- or t-butylamino, dimethylamino, diethylamino, dipropylamino or dibutylamino, or represents cyclopropyl, cyclobutyl, cyclopentyl, cyclohexyl, cyclopropylmethyl, cyclobutylmethyl, cyclopentylmethyl, cyclohexylmethyl, cyclohexylethyl or cyclohexylpropyl, each of which is optionally substituted by fluorine, chlorine, bromine, cyano, methyl, ethyl, n- or i-propyl or represents benzyl, phenylethyl, phenylpropyl, phenylbutyl, phenylethenyl, phenylpropenyl, phenylbutenyl, phenylethinyl, phenylpropinyl or phenyl-butinyl, each of which is optionally substituted by fluorine, chlorine, bromine, cyano, methyl, ethyl, n- or i-propyl, n-, i-, s- or t-butyl, methoxy or ethoxy, (c) alkylanilines such as, for example, N-(1-ethyl-propyl)-3,4-dimethyl-2,6-dinitro-aniline (pendimethalin) or N,N-dipropyl-2,6-dinitro-4-trifluoromethyl-aniline (trifluralin);

(d) carboxylic acids such as, for example, 3,6-dichloro-pyridine-2-carboxylic acid (clopyralid), 2,4-dichloro-phenoxy acetic acid (2,4-D), 3,6-dichloro-2-methoxy-benzoic acid (dicamba), 4-amino-3,5-dichloro-6-fluoro-pyridin-2-yl-oxy-acetic acid (fluroxypyr), ammonium 2-amino-4-(hydroxymethylphosphinyl)-butanoate (glufosinate-ammonium), N-phosphonomethyl-glycine (glyphosate), 2-(4,5-dihydro-4-methyl-4-i-propyl-5-oxo-1H-imidazol-2-yl)-5-ethyl-pyridine-3-carboxylic acid (imazethapyr) or 2-(4,5-dihydro-4-methyl-4-i-propyl-5-oxo-1H-imidazol-2-yl)-quinoline-3-carboxylic acid (imazaquin);

(e) carboxamides, such as, for example, N-(2-methoxy-1-methyl-ethyl)-N-(2-ethyl-6-methyl-phenyl)-2-chloro-acetamide (metolachlor), N-ethoxymethyl-N-(2-ethyl-6-methyl-phenyl)-2-chloro-acetamide (acetochlor), N-methoxymethyl-N-(2,6-dimethyl-phenyl)-2-chloro-acetamide (alachlor), N-(2-methoxy-1-methyl-ethyl)-N-(2,4-dimethyl-3-thienyl)-2-chloroacetamide (dimethanamid), N-(1H-pyrazol-1-yl-methyl)-N-(2,6-dimethylphenyl)-2-chloro-acetamide (metazachlor) or N-i-propyl-N-phenyl-2-chloro-acetamide (propachlor);

(f) diazin(on)es, or triazin(on)es, such as, for example, 2-chloro-4-ethylamino-6-i-propylamino-1,3,5-triazine (atrazine), 3-i-propyl-1H-2,1,3-benzothiadiazin-4(3H)-one 2,2-dioxide (bentazone), 2-chloro-4-ethylamino- 6-(1-cyano-1-methyl-ethylamino)-1,3,5-triazine (cyanazine), 4-amino-6-t-butyl-4,5-dihydro-3-methylthio-1,2,4-triazin-5-one (metribuzin), O-(6-chloro-3-phenyl-4-pyridazinyl) S-octyl thiocarbonate (pyridate); 2-chloro-4,6-bis-ethylamino-1,3,5-triazine (simazine) or 2-chloro-4-ethylamino-6-t-butylamino-1,3,5-triazine (terbuthylazine);

(g) ureas, such as, for example, N-(4,6-dimethoxy-pyrimidin-2-yl)-N'-(3-chloro-4-methoxycarbonyl-1-methyl-pyrazol-5-yl-sulphonyl)-urea (clopyrasulfurone), N-methoxy-N-methyl-N'-[4-(3,4-dihydro-2-methoxy-2,4,4-trimethyl-2H-1-benzopyran7-yl-oxy)-phenyl]-urea (metobenzuron), N-(4,6-dimethoxy-pyrimidin-2-yl)-N'-(3-dimethylaminocarbonyl-pyridin-2-yl-sulphonyl)-urea (nicosulfuron), N-(4,6-bis-difluoromethoxypyrimidin-2-yl)-N'-(2-methoxycarbonyl-phenylsulphonyl)-urea (primisulfuron-methyl),N-(4-methoxy-6-methyl-1,3,5-triazin-2-yl)-N'-[2-(3,3,3-trifluoro-propyl)-phenylsulphonyl]-urea (prosulfuron), N-(4,6-dimethoxypyrimidin-2-yl)-N'-(3-ethylsulphonyl-pyridin-2-yl-sulphonyl)-urea (rimsulfuron) or N-(4-methoxy-6-methyl-1,3,5-triazin-2-yl)-N'-(2-methoxycarbonyl-3-thienyl-sulphonyl)-urea (thifensulfuron-methyl);

(h) nitriles such as, for example, 3,5-dibromo4-hydroxy-benzonitrile (bromoxynil) or 3,5-diiod4-hydroxy-benzonitrile (ioxynil);

(i) thiocarbamates such as, for example, S-ethyl di-i-butylthiocarbamate (butylate) or S-ethyl dipropylthiocarbamate (EPTC);

(j) active compounds from a variety of substance groups such as, for example, N-2,6-difluoro-phenyl-5-methyl-[1,2,4]-triazolo-[1,5-a]-pyrimidine-2-sulphonamide (flumetsulam), 1,1'-dimethyl4,4'-bipyridinium chloride (paraquat) or 2-(2-chloro4-methylsulphonylbenzoyl)-1,3-cyclohexanedione (sulcotrione), in each case 0.1 to 10 parts by weight of active compound of the general formula (II) preferably being used per part by weight of active compound of the general formula (I).

The following may be mentioned as individual examples of the compounds of the formula (I) to be used as components in mixtures according to the invention:

1-(4-chloro-3-methylsulphonylamino-phenyl)-3,6-dihydro-2,6-dioxo-3-methyl-4-trifluoromethyl-1(2H)-pyrimidine, 1-(4-chloro-3-methylsulphonylamino-phenyl)-3,6-dihydro-2,6-dioxo-3-amino-4-trifluoromethyl-1(2H)-pyrimidine, 1-(4-cyano-3-methylsulphonylamino-phenyl)-3,6-dihydro-2,6-dioxo-3-methyl-4-trifluoromethyl-1(2H)-pyrimidine, 1-(4-chloro-3-ethylsulphonylamino-phenyl)-3,6-dihydro-2,6-dioxo-3-methyl-4-trifluoromethyl-1(2H)-pyrimidine, 1-(4-chloro-3-ethylsulphonylamino-phenyl)-3,6-dihydro-2,6-dioxo-3-amino-4-trifluoromethyl-1(2H)-pyrimidine, 1-(4-cyano-3-ethylsulphonylamino-phenyl)-3,6-dihydro-2,6-dioxo-3-methyl-4-trifluoromethyl-1(2H)-pyrimidine, 1-(4-chloro-3-n-propylsulphonylamino-phenyl)-3,6-dihydro-2,6-dioxo-3-methyl-4-trifluoromethyl-1(2H)-pyrimidine, 1-(4-chloro-3-n-propylsulphonylamino-phenyl)-3,6-dihydro-2,6-dioxo-3-amino-4-trifluoromethyl-1(2H)-pyrimidine, 1-(4-cyano-3-n-propylsulphonylamino-phenyl)-3,6-dihydro-2,6-dioxo-3-methyl-4-trifluoromethyl-1(2H)-pyrimidine, 1-(4-chloro-3-i-propylsulphonylamino-phenyl)-3,6-dihydro-2,6-dioxo-3-methyl4-trifluoromethyl-1(2H)-pyrimidine, 1-(4-chloro-3-i-propylsulphonylamino-phenyl)-3,6-dihydro-2,6-dioxo-3-amino4-trifluoromethyl-1(2H)-pyrimidine, 1-(4-cyano-3-i-propylsulphonylamino-phenyl)-3,6-dihydro-2,6-dioxo-3-methyl-4-trifluoromethyl-1(2H)-pyrimidine, 1-(4-chloro-5-methylsulphonylamino-2-fluoro-phenyl)-3,6-dihydro-2,6-dioxo-3-methyl-4-trifluoromethyl-1(2H)-pyrimidine, 1-(4-chloro-5-methylsulphonylamino-2-fluoro-phenyl)-3,6-dihydro-2,6-dioxo-3-amino-4-trifluoromethyl-1(2H)-pyrimidine, 1-(4-cyano-5-methylsulphonylamino-2-fluoro-phenyl)-3,6-dihydro-2,6-dioxo-3-methyl-4-trifluoromethyl-1(2H)-pyrimidine, 1-(4-chloro-5-ethylsulphonylamino-2-fluoro-phenyl)-3,6-dihydro-2,6-dioxo-3-methyl-4-trifluoromethyl-1(2H)-pyrimidine, 1-(4-chloro-5-ethylsulphonylamino-2-fluoro-phenyl)-3,6-dihydro-2,6-dioxo-3-amino-4-trifluoromethyl-1(2H)-pyrimidine, I-(4-cyano-5-ethylsulphonylamino-2-fluoro-phenyl)-3,6-dihydro-2,6-dioxo-3-methyl-4-trifluoromethyl-1(2H)-pyrimidine, 1-(4-chloro-5-n-propylsulphonylamino-2-fluoro-phenyl)-3,6-dihydro-2,6-dioxo-3-methyl-4-trifluoromethyl-1(2H)-pyrimidin, 1-(4-chloro-5-n-propylsulphonylamino-2-fluor-phenyl)-3,6-dihydro-2,6-dioxo-3-amino-4-trifluoromethyl-1(2H)-pyrimidine, 1-(4-cyano-5-n-propylsulphonylamino-2-fluoro-phenyl)-3,6-dihydro-2,6-dioxo-5-methyl4-trifluoromethyl-1(2H)-pyrimidine, 1-(4-chloro-5-i-propylsulphonylamino-2-fluoro-phenyl)-3,6-dihydro-2,6-dioxo-3-methyl-4-trifluoromethyl-1(2H)-pyrimidine, 1-(4-chloro-5-i-propylsulphonylamino-2-fluoro-phenyl)-3,6-di-5-hydro-2,6-dioxo-3-amino-4-trifluoromethyl-1(2H)-pyrimidine, 1-(4-cyano-5-i-propylsulphonylamino-2-fluoro-phenyl)-3,6-dihydro-2,6-dioxo-3-methyl-4-trifluoromethyl-1(2H)-pyrimidine, 1-(4-cyano-5-n-butylsulphonylamino-2-fluoro-phenyl)-3,6-dihydro-2,6-dioxo-3-methyl-4-4-trifluoromethyl-1(2H)-pyrimidine.

The following may be mentioned as individual examples of compounds of the formula (II) to be used as components in mixtures according to the invention:

N-methyl-N-phenyl-α-(5-trifluoromethyl-1,3,4-thiadiazol-2-yl-oxy)-acetamide, N-ethyl-N-phenyl-α-(5-trifluoromethyl-1,3,4-thiadiazol-2-yl-oxy)-acetamide, N-n-propyl-N-phenyl-α-(5-trifluoromethyl-1,3,4-thiadiazol-2-yl-oxy)-acetamide, N-i-propyl-N-phenyl-α-(5-trifluoromethyl-1,3,4-thiadiazol-2-yl-oxy)-acetamide, N-methyl-N-(4-fluoro-phenyl)-α-(5-trifluoromethyl-1,3,4-thiadiazol-2-yl-oxy)-acetamide , N-ethyl-N-(4-fluoro-phenyl)-α-(5-trifluoromethyl-1,3,4-thiadiazol-2-yl-oxy)-acetamide, N-n-propyl-N-(4-fluoro-phenyl)-α-(5-trifluoromethyl-1,3,4-thiadiazol -2-yl -oxy)-acetamide, N-i-propyl-N-(4-fluoro-phenyl)-α-(5-trifluoromethyl 1,3,4-thiadiazol-2-yl-oxy) -acetamide, N-methyl-N-(4-chloro-phenyl)-α-(5-trifluoromethyl-1,3,4-thiadiazol-2-yl-oxy) acetamide, N-ethyl-N-(4-chloro-phenyl)-α-(5-trifluoromethyl-1,3,4-thiadiazol-2-yl-oxy)-acetamide, N-n-propyl-N-(4-chloro-phenyl)-α-(5-trifluoromethyl-1,3,4-thiadiazol-2-yl-oxy)-acetamide and N-i-propyl-N-(4-chloro-phenyl)-α-(5-trifluoromethyl-1,3,4-thiadiazol-2-yl-oxy)-acetamide.

The following may be mentioned as individual examples of the compounds of the formula (III) to be used as components in mixtures according to the invention:
4-amino-5-methyl-2-(1,1-dimethyl-ethyl-aminocarbonyl)-2,4-dihydro-3H-1,2,4-triazol-3-one, 4-amino-5-ethyl-2-(1,1-dimethyl-ethyl-aminocarbonyl)-2,4-dihydro-3H-1,2,4-triazol-3-one, 4-amino-5-n-propyl-2-(1,1-dimethyl-ethyl-aminocarbonyl)-2,4-dihydro-3H-1,2,4-triazol-3-one, 4-amino-5-i-propyl-2-(1,1-dimethyl-ethyl-aminocarbonyl)-2,4-dihydro-3H-1,2,4-triazol-3-one, 4-amino-5-methoxy-2-(1,1-dimethyl-ethyl-aminocarbonyl)-2,4-dihydro-3H-1,2,4-triazol-3-one, 4-amino-5-ethoxy-2-(1,1-dimethylethyl-aminocarbonyl)-2,4-dihydro-3H-1,2,4-triazol-3-one, 4-amino-5-methyl-2-(2-fluoro-1,1-dimethyl-ethyl-aminocarbonyl)-2,4-dihydro-3H-1,2,4-triazol-3-one, 4-amino-5-ethyl-2-(2-fluoro-1,1-dimethyl-ethyl-aminocarbonyl)-2,4-dihydro-3H-1,2,4-triazol-3-one, 4-amino-5-n-propyl-2-(2-fluoro-1,1-dimethyl-ethyl-aminocarbonyl)-2,4-dihydro-3H-1,2,4-triazol-3-one, 4-amino-5-i-propyl-2-(2-fluoro-1,1-dimethyl-ethylaminocarbonyl)-2,4-dihydro-3H-1,2,4-triazol-3-one, 4-amino-5-methoxy-2-(2-fluoro-1,1-dimethyl-ethyl-aminocarbonyl)-2,4-dihydro-3H-1,2,4-triazol-3-one, 4-amino-S-ethoxy-2-(2-fluoro-1,1-dimethyl-ethyl-aminocarbonyl)-2,4-dihydro-3H-1,2,4-triazol-3-one, 4-amino-5-methyl-2-(2-chloro-1,1-dimethyl-ethylaminocarbonyl)-2,4-dihydro-3H-1,2,4-triazol-3-one, 4-amino-5-ethyl-2-(2-chloro-1,1-dimethyl-ethyl-aminocarbonyl)-2,4-dihydro-3H-1,2,4-triazol-3-one, 4-amino-5-n-propyl-2-(2-chloro-1,1-dimethyl-ethyl-aminocarbonyl)-2,4-dihydro-3H-1,2,4-triazol-3-one, 4-amino-5-i-propyl-2-(2-chloro-1,1-dimethyl-ethyl-aminocarbonyl)-2,4-dihydro-3H- 1,2,4-triazol-3-one, 4-amino-5-methoxy-2-(2-chloro-1,1-dimethyl-ethyl-aminocarbonyl)-2,4dihydro-3H-1,2,4-triazol-3-one, 4-amino-5-ethoxy-2-(2-chloro-1,1-dimethyl-ethyl-aminocarbonyl)-2,4-dihydro-3H-1,2,4-triazol-3-one, 4-amino-5-i-propyl-2-i-propyl-aminocarbonyl-2,4-dihydro-3H-1,2,4-triazol-3-one, 4-amino-5-dimethylamino-2-(1,1-dimethyl-ethyl-aminocarbonyl)-2,4-dihydro-3H-1,2,4-triazol-3-one, 4-amino-5-dimethylamino-2-(2-fluoro-1,1-dimethyl-ethyl-aminocarbonyl)-2,4-dihydro-3H-1,2,4-triazol-3-one, 4-amino-5-dimethylamino-2-(2-chloro-1,1-dimethyl-ethyl-aminocarbonyl)-2,4-dihydro-3H-1,2,4-triazol-3-one and 4-methyl-5-methoxy-2-(1,1-dimethyl-ethyl-aminocarbonyl)-2,4-dihydro-3H-1,2,4-triazol-3-one.

The compounds of the formula (I) are described in the abovementioned patent applications or patent specifications.

The compounds of the formula (II) are known and/or can be prepared by known methods (cf. EP-A 5501, EP-A 18497, EP-A 29171, EP-A 94514, EP-A 100044, EP-A 100045, EP-A 161602, EP-A 195237, EP-A 348734, EP-A 348737).

The compounds of the formula (III) are also known and/or can be prepared by known methods (cf. EP-A 294666, EP-A 370293, EP-A 391187, EP-A 398096, EP-A 399294, EP-A 415196, EP-A 477646).

Surprisingly, it has now been found that the above-defined active compound combinations of the aryluracils (or arylthiouracils) of the formula (I) and the active compounds mentioned above under group 2 exhibit a particularly high herbicidal activity and can be used for selective weed control in a variety of crops, in particular in maize, but also in soya beans, sunflowers, wheat, barley and sugar cane.

Surprisingly the herbicidal activity of the active compound combinations according to the invention considerably exceeds the sum of the activities of the individual active compounds.

This means that not only a complementation of action is present, but the true synergistic effect, which could not have been anticipated. The new active compound combinations are well tolerated by a series of crops such as, for example, in maize, soya beans and sugar cane, and even weeds which are otherwise a problem are controlled by the new active compound combinations. The new active compound combinations are therefore a valuable enrichment of the selective herbicides, in particular of the herbicides which can be used in maize.

The following may be mentioned as examples of weeds which can be controlled efficiently with the active compound combinations according to the invention:

Dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Solanum, Cirsium, Carduus, Sonchus, Rorippa, Rotala, Lindernia, Lamium, Veronica, Abutilon, Emex, Sida, Datura, Viola, Galeopsis, Papaver, Centaurea, Trifolium, Ranunculus, Taraxum.

Monocotyledon weeds from the genera Echinochloa, Setaria, Panicum, Digitaria, Phleum, Poa, Festuca, Eleusine, Brachiaria, Lolium, Bromus, Avena, Cyperus, Sorhum, Agropyron, Cynodon, Monochoria, Fimbristylis, Sagittaria, Eleocharis, Scirpus, Papalum, Ischaemum, Sphenoclea, Dactylocenium, Agrostis, Alopecurus, Apera.

However, the use of the active compound combinations according to the invention is in no way restricted to these genera, but also extends in the same manner to other plants.

As already indicated, the active compound combinations according to the invention are not only highly compatible with maize crops, but also have an outstanding activity against broad-leaved weeds and grass weeds. The possibility of using them as selective herbicides in maize may therefore be particularly emphasized.

The synergistic effect of the active compound combinations according to the invention is especially pronounced at specific concentration ratios. However, the weight ratios of the active compounds in the active compound combinations can be varied within relatively wide ranges. In general, 0.001 to 1000 parts by weight, preferably 0.01 to 100 parts by weight, especially preferably 0.1 to 10 parts by weight, of active compound of group 2 are used per part by weight of active compound of group 1.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are for example: for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolyzates; suitable dispersants are: for example lignin-sulphite waste liquors and methylcellulose.

Adhesives such as carboxymethylcellulose and natural and synthetic polymers in the form of powders, granules or latexes such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

In general, the active compound combinations according to the invention are applied in the form of ready mixes. However, the active compound in the active compound combinations can also be formulated individually and mixed upon application, that is to say applied in the form of tank mixes.

The new active compound combinations as such or in the form of their formulations, can also be used as mixtures with further known maize herbicides for controlling weeds, finished formulations or tank mixes being possible. Mixtures with other known active compounds such as fungicides, insecticides, acaricides, nematicides, bird repellants, growth promoters, plant nutrients and soil conditioners, are also possible. Furthermore, it may be advantageous for specific purposes, in particular when using the post-emergence method, to incorporate mineral or vegetable oils (for example "Oleo Dupont 11E", which is commercially available) or ammonium salts such as, for example, ammonium sulphate or ammonium thiocyanate which are tolerated by plants, as further additives in the formulations.

The active compound combinations according to the invention can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or spreading.

The active compound combinations according to the invention can be applied either before or after emergence of the plants. They can also be incorporated into the soil before sowing.

The active compound combinations according to the invention can be applied (a) in conventional maize growing ("conventional tillage"), both pre- and post-emergence, or (b) in soil-preserving maize growing ("pre-plant burndown").

Suitable components in mixtures for conventional growing which may be emphasized are especially the following, known active compounds—the names given are in each case "common names" or replaced by known codes:
acetochlor, alachlor, atrazinee, bentazone, butylate, clopyralid, cyanazinee, 2,4-D, dimetheneamide, EPTC, flumetsulam, fluroxypyr, clopyrasulfuron, imazethapyr, imazaquin, ioxynil, metazachlor, metobenzuron, metolachlor, metribuzin, nicosulfuron, pendimethalin, primisulfuron, propachlor, prosulfuron, pyridate, rimsulfuron, simazine, sulcotrione, terbutylazine, thifensulfuron, trifluralin.

Known active compounds which may be emphasized particularly as suitable components in mixtures for soil-preserving cultivation are the following:
bentazone, bromoxynil, dicamba, 2,4-D, glyphosate, metribuzin, paraquat, diquat, glufosinate.

The rates of application of the active compound combinations according to the invention can be varied within a substantial range. They depend essentially on the nature of the desired effect. In general, the rates of application are between 10 g and 10 kg of active compound combination per hectate of soil surface, preferably between 50 g and 5 kg per ha, in particular between 100 g and 2 kg per ha.

While the individual active compounds show weaknesses in their herbicidal activity, the combinations according to the invention all show very efficient and broadly effective control of the weeds which are mainly found in maize, and this control exceeds a simple sum of the activities.

In herbicides, a synergistic effect is always present when the herbicidal activity of the active compound combination exceeds that of the active compounds applied individually.

The expected activity for a given combination of two herbicides can be calculated as follows (cf. Colby, S. R.; "Calculating synergistic and antagonistic responses of herbicide combinations", Weeds 15, pages 20–22, 1967):
If
X=% damage by herbicide A (active compound of group 1) at the rate of application of p kg/ha and
Y=% damage by herbicide B (active compound of group 2) at the rate of application of q kg/ha and
E=the expected damage caused by herbicides A and B at a rate of application of p and q kg/ha,
then $$E = X + Y - (X*Y/100).$$

If the actual damage exceeds the calculated value, the combination is super additive with regard to its activity, i.e. it shows a synergistic effect.

Use experiments with the active compound combinations according to the invention reveal that the herbicidal activity of the active compound combinations according to the invention exceeds the calculated value, i.e. that the new active compound combinations have a synergistic action.

We claim:

1. Herbicidal compositions comprising an effective amount of an active compound combination composed of (1) an aryluracil, or an aryl-thiouracil, of the formula (I)

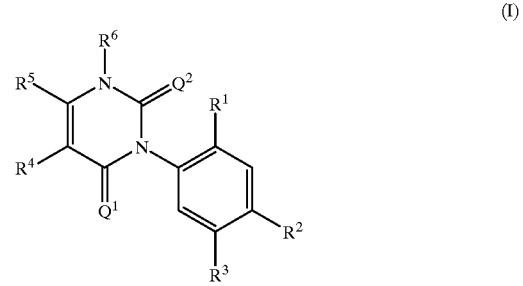

or a compound of the formula (Ia) which is isomeric thereto

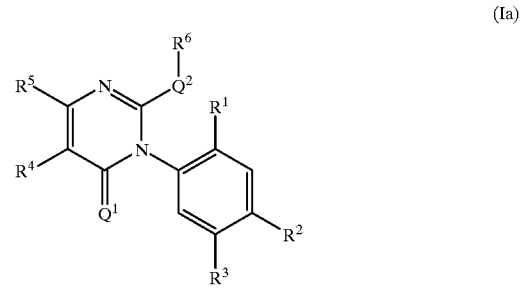

in which $Q^1$ represents oxygen or sulphur,
$Q^2$ represents oxygen or sulphur,
$R^1$ represents hydrogen, fluorine, chlorine or bromine,
$R^2$ represents cyano,
$R^3$ represents the group below,

-$A^1$-$A^2$-$A^3$ in which
$A^1$ represents oxygen, sulphur, or the group —N-$A^4$- in which $A^4$ is hydrogen, hydroxyl, $C_1$–$C_4$-alkyl, $C_1$–$C_4$-alkoxy, phenyl, $C_1$–$C_4$-alkylsulphonyl or phenylsulphonyl,
$A^2$ represents a single bond, or represents —CO—,
$A^3$ represents hydrogen, or represents alkyl, which has 1 to 6 carbon atoms and which is optionally substituted by halogen or $C_1$–$C_4$-alkoxy, or represents alkenyl, alkenyloxy, alkenyloxycarbonyl, alkinyl, alkinyloxy, or alkinyloxycarbonyl, each of which has 2 to 6 carbon atoms in the alkenyl or alkinyl groups and each of which is optionally substituted by halogen, or represents phenyl, which is optionally substituted by nitro, cyano, carboxyl, halogen $C_1$–$C_4$-alkyl, $C_1$–$C_4$-halogenoalkyl, $C_1$–$C_4$-alkoxy, $C_1$–$C_4$-halogeonalkoxy and/or $C_1$–$C_4$-alkoxycarbonyl, or heterocyclyl or (in each case optionally fully or partially hydrogenated) thienyl, oxazolyl, thienyl-$C_1$–$C_4$-alkyl or oxazolyl-$C_1$–$C_4$-alkyl,
$R^4$ represents hydrogen, fluorine, chlorine, bromine, or alkyl having 1 to 4 carbon atoms which is optionally substituted by fluorine and/or chlorine,
$R^5$ represents hydrogen, fluorine, chlorine, bromine, or alkyl having 1 to 4 carbon atoms which is optionally substituted by fluorine and/or chlorine, and
$R^6$ represents hydrogen, hydroxyl, amino, or represents alkyl, alkoxy, alkenyl or alkinyl, each of which has up to 4 carbon atoms and each of which is optionally substituted by fluorine, chlorine or cyano, and
(2) an active compound from the second group of herbicides which contains the compound classes (a) to (j) given below:
(a) heteroaryloxyacetamides of the formula (II)

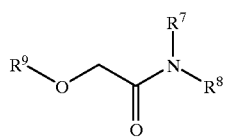

(II)

in which
$R^7$ represents alkyl, alkenyl, alkinyl or alkoxy, each of which has up to 6 carbon atoms and each of which is optionally substituted by halogen, cyano or $C_1$–$C_4$-alkoxy,
$R^8$ represents alkyl, alkenyl or alkinyl, each of which has up to 6 carbon atoms and each of which is optionally substituted by halogen, cyano or $C_1$–$C_4$-alkoxy, or represents phenyl which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy, and
$R^9$ represents heteroaryl from the series consisting of 1,3-thiazol-2-yl, 1,2,4-thiadiazol-5-yl, 1,3,4-thiadiazol-2-yl, benzoxazol-2-yl, benzothiazol-2-yl, each of which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy;

(b) carbamoyltriazolinones of the formula (III)

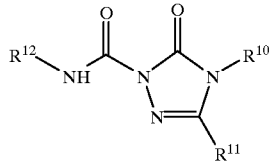

(III)

in which
$R^{10}$ represents hydrogen, hydroxyl, amino, or represents alkyl, alkenyl, alkinyl, alkoxy, alkenyloxy, alkinyloxy, alkylamino, alkenylamino, alkinylamino, alkylideneamino or dialkylamino, each of which has up to 6 carbon atoms and each of which is optionally substituted by halogen or cyano, or represents cycloalkyl, cycloalkylalkyl, each of which has 3 to 6 carbon atoms in the cycloalkyl groups and, 1 to 4 carbon atoms in the alkyl group and each of which is optionally substituted by halogen, cyano or $C_1$–$C_4$-alkyl, or represents phenyl or phenyl-$C_1$–$C_4$-alkyl, each of which is optionally substituted by halogen, cyano, $C_1$–$C_4$-alkyl or $C_1$–$C_4$-alkoxy,
$R^{11}$ represents alkyl, alkenyl, alkinyl, alkoxy, alkenyloxy, alkinyloxy, alkylthio, alkenylthio, alkinylthio, alkylamino, alkenylamino, alkinylamino or dialkylamino, each of which has up to 6 carbon atoms and each of which is optionally substituted by halogen, cyano, $C_1$–$C_4$-alkoxy or $C_1$–$C_4$-alkylthio, or represents cycloalkyl, cycloalkyloxy or cycloalkylalkyl, each of which has 3 to 6 carbon atoms in the cycloalkyl groups and, 1 to 4 carbon atoms in the alkyl group and each of which is optionally substituted by halogen, cyano or $C_1$–$C_4$-alkyl, or represents phenyl, phenoxy, phenylthio, phenylamino or phenyl-$C_1$–$C_4$-alkyl, each of which is optionally substituted by halogen, cyano, $C_1$–$C_4$-alkyl or $C_1$–$C_4$-alkoxy, and
$R^{12}$ represents alkyl, alkenyl, alkinyl, each of which has up to 10 carbon atoms and each of which is optionally substituted by halogen, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–C4-alkylamino or di-($C_1$–$C_4$-alkyl)-amino, or represents cycloalkyl or cycloalkylalkyl, each of which has 3 to 6 carbon atoms in the cycloalkyl moiety and,
1 to 4 carbon atoms in the alkyl moiety and each of which is optionally substituted by halogen, cyano or $C_1$–$C_4$-alkyl, or represents phenyl-C-$C_6$-alkyl, phenyl-$C_2$–$C_6$-alkenyl or phenyl-$C_2$–$C_6$-alkinyl, each of which is optionally substituted by halogen, cyano, $C_1$–$C_4$-alkyl or $C_1$–$C_4$-alkoxy;
(c) alkylanilines comprising N-(1-ethyl-propyl)-3,4-dimethyl-2,6-dinitro-aniline(pendimethalin) or N,N-dipropyl-2,6-dinitro-4-trifluoromethyl-aniline (trifluralin);
(d) carboxylic acids comprising 3,6-dichloro-pyridine-2-carboxylic acid (clopyralid), 2,4-dichloro-phenoxy acetic acid (2,4-D), 3,6-dichloro-2-methoxy-benzoic acid (dicamba), 4-amino-3,5-dichloro-6-fluoro-pyridin-2-yl-oxy-acetiacid (fluroxypyr), ammonium 2-amino-4-(hydroxymethylphosphinyl)butanoate (glufosinate-ammonium), N-phosphonomethyl-glycine (glyphosate), 2-(4,5-dihydro-4-methyl-4-i-propyl-5-oxo-1H-imidazol-2-yl)-5ethyl-pyridine-3-carboxylic acid (imazethapyr) or 2-(4, 5-dihydro-4-methyl-4-i-propyl-5-oxo- H-imidazol-2-yl) quinoline-3-carboxylic acid (imazaquin);

(e) carboxamides comprising N-(2-methoxy-1-methyl-ethyl)-N-(2-ethyl-6-methylphenyl)-2-chloro-acetamide (metolachlor), N-ethoxymethyl-N-(2-ethyl-6-methyl-ethyl)-2-chloroacetamide (acetochlor), N-methoxymethyl-N-(2,6-dimethyl-phenyl)-2-chloro-acetamide (alachlor), N-(2-methoxy-1-methylethyl)-N-(2,4-dimethyl-3-theinyl)-2-chloro-acetamide (dimethanamid), N-(1H-pyrazol-1-yl-methyl)-N-(2, 6-dimethyl-phenyl)-2-chloro-acetamide (metazachlor) or N-i-propyl-N-phenyl-2-chloro-acetamide (propachlor);

(f) diazin(on)es, or triazin(on)es comprising 2-chloro-4-ethylamino-6-i-propylamino-1,3,5-triazine (atrazine), 3-i-propyl-1H-2,1,3-benzothiadiazin-4(3H)-one 2,2-dioxide (bentazone), 2-chloro-4-ethylamino-6-(1-cyano-1-methyl-ethylamino)1,3,5-triazine (cyanazine), 4-amino-6-t-butyl-4,5-dihydro-3-methylthio-1,2,4-triazin-5-one (metribuzin), O-(6-chloro-3-phenyl4-pyridazinyl) S-octyl thiocarbonate (pyridate); 2-chloro-4,6-bis-ethylamino-1,3,5-triazine (simazine) or 2-chloro-4-ethylamino-6-t-butylamino-1,3,5-triazine (terbuthylazine);

(g) ureas comprising N-(4,6-dimethoxy-pyrimidin-2-yl)-N-(3-chloro-4-methoxycarbonyl-1-methyl-pyrazol-5-yl-sulphonyl)-urea (clopyrasulfurone), N-methoxy-N-methyl-N'-[4-(3,4-dihydro-2-methoxy-2,4,4-trimethyl-2H-1-benzopyran 7-yl-oxy)phenyl]-urea (metobenzuron), N-(4,6,-dimethoxy-pyrmidin-2-yl)-N'-(3-dimethylaminocarbonyl-pyridin-2-yl-sulphonyl)-urea (nicosulfuron), N-(4,6-bis-difluoromethoxy-pyrimidin-2-yl)-N'-(2-methoxycarbonyl-phenylsulphonyl)-urea (primisulfuron-methyl), N-(4-methoxy-6-methyl-1,3,5-triazin-2-yl)-N'-[2-(3,3,3-trifluoropropyl)-phenylsulphonyl]-urea (prosulfuron), N-(4,6-dimethoxypyrimidin-2-yl)-N'-(3-ethylsulphonyl-pyridin-2-yl-sulphonyl)-urea (rimsulfuron)or N-(4-methoxy-6-methyl-1,3,5-triazin-2-yl)-N'-(2-methoxycarbonyl-3-thienyl-sulphonyl)-urea (thifensulfuron-methyl);

(h) nitriles comprising 3,5-dibromo-4-hydroxy-benzonitile (bromoxynil) or 3,5-diiod-4-hydroxy-benzonitrile (ioxynil);

(i) thiocarbamates comprising S-ethyl N-di-i-butylthiocarbamate (butylate) or S-ethyl N-dipropylthiocarbamate (EPTC);

(j) active compounds from a variety of substance groups comprising N-2,6-difluoro-phenyl-5-methyl-[1,2,4]-triazolo-[1,5-a]-pyrimidine-2-sulphonamide (flumetsulam), 1,1'-dimethyl-4,4'-bipyridinium chloride (paraquat) or 2-(2-chloro-4-methyl-sulphonyl-benzoyl)-1,3-cyclohexanedione (sulcotrione).

2. Herbicidal compositions according to claim 1, wherein the active compound combination is composed of (1) a compound of the formula (I) or (Ia) in which $Q^1$ represents oxygen or sulphur, $Q^2$ represents oxygen or sulphur, $R^1$ represents hydrogen, fluorine, chlorine or bromine, $R^2$ represents cyano, $R^3$ represents the group below,

-A¹-A²-A³ in which $A^1$ represents oxygen, sulphur, or the group —N-$A^4$- where $A^4$ represents hydrogen, hydroxyl, methyl, ethyl, n- or i-propyl, methoxy, ethoxy, n- or i-propoxy, methylsulphonyl or ethylsulphonyl, $A^2$ represents a single bond, or represents —CO—, $A^3$ represents hydrogen, or represents in each case optionally fluorine-, chlorine-, methoxy- or ethoxy- substituted methyl, ethyl, n- or i-propyl, n-, i-, s- or t-butyl, n-, i-, s- or t-pentyl, or represents propenyl, butenyl, propenyloxy, butenyloxy, propenyloxycarbonyl, butenyloxycarbonyl, propinyl, butinyl, propinyloxy, butinyloxy, propinyloxycarbonyl or butinyloxycarbonyl, each of which is optionally substituted by fluorine or chlorine, or represents in each case optionally nitro-, cyano-, carboxyl, fluorine-, chlorine-, bromine-, methyl-, ethyl-, n- or i-propyl, trifluoromethyl-, methoxy-, ethoxy-, n- or i-propoxy, difluoromethoxy-, trifluoromethoxy-, methoxycarbonyl- and/or ethoxycarbonyl- substituted phenyl, or heterocyclyl or (in each case optionally fully or partially hydrogenated) thienyl, oxazolyl, thienylmethyl, oxazolylmethyl, $R^4$ represents hydrogen, fluorine, chlorine, or represents methyl or ethyl, each of which is optionally substituted by fluorine and/or chlorine, $R^5$ represents hydrogen, fluorine, chlorine, or represents methyl or ethyl, each of which is optionally substituted by fluorine, and/or chlorine, and $R^6$ represents hydrogen, hydroxyl, amino, or represents methyl, ethyl, n- or i-propyl, methoxy, ethoxy, n- or i-propoxy, propenyl or propinyl, each of which is optionally substituted by fluorine, chlorine or cyano, and (2) an active compound from a second group of herbicides which contains the compound classes (a) to (j) given below:

(a) heteroaryloxyacetamides of the formula (II) in which $R^7$ represents methyl, ethyl, n- or i-propyl, n-, i- or s-butyl, propenyl, butenyl, propinyl, butinyl, methoxy, ethoxy, n- or i-propoxy, n-, i-, s- or t-butoxy, each of which is optionally substituted by fluorine, chlorine, cyano, methoxy or ethoxy, $R^8$ represents methyl, ethyl, n- or i-propyl, n-, i-, s- or t-butyl, n-, i-, s- or t-pentyl, propenyl, butenyl, propinyl or butinyl, each of which is optionally substituted by fluorine, chlorine, cyano, methoxy or ethoxy, or represents phenyl which is optionally substituted by fluorine, chlorine,. bromine, cyano, methyl, ethyl, trifluoromethyl, methoxy, ethoxy, difluoromethoxy or trifluoromethoxy, and $R^9$ represents heteroaryl from the series consisting of 1,3-thiazol-2-yl, 1,2,4-thiadiazol-5-yl, 1,3,4-thiadiazol-2-yl, benzoxazol-2-yl, benzothiazol-2-yl, each of which is optionally substituted by fluorine, chlorine, bromine, cyano, methyl, ethyl, n- or i-propyl, n-, i-, s- or t-butyl, difluoromethyl, trifluoromethyl, dichloromethyl, trichloromethyl, methoxy, ethoxy, n- or i-propoxy, n-, i-, s- or t-butoxy, difluoromethoxy or trifluoromethoxy;

(b) carbamoyltriazolinones of the formula (III) in which $R^{10}$ represents hydrogen, hydroxyl, amino, or represents methyl, ethyl, n- or i-propyl, n-, i-, s- or t-butyl, propenyl, butenyl, propinyl or butinyl, methoxy, ethoxy, n- or i-propoxy, n-, i-, s- or t-butoxy, propenyloxy, butenyloxy, propinyloxy or butinyloxy, methylamino, ethylamino, n- or i-propylamino, n-, i-, s- or t-butylamino, propenylamino, butenylamino, propinylamino or butinylamino, ethylideneamino, propylideneamino, butylideneamino, dimethylamino or diethylamino, each of which is optionally substituted by fluorine, chlorine or cyano, or represents cyclopropyl, cyclobutyl, cyclopentyl, cyclohexyl, cyclopropylmethyl, cyclobutylmethyl, cyclopentylmethyl or cyclohexylmethyl, each of which is optionally substituted by fluorine, chlorine, bromine, cyano, methyl, ethyl, n- or i-propyl, or represents phenyl or benzyl, each of which is optionally substituted by fluorine, chlorine, bromine, cyano, methyl, ethyl, n- or i-propyl, n-, i-, s- or t-butyl, methoxy or ethoxy, $R^{11}$ represents methyl, ethyl, n- or i-propyl, n-, i-, s- or t-butyl, propenyl, butenyl, propinyl, butinyl, methoxy, ethoxy, n- or i-propoxy, n-, i-, s- or t-butoxy, propenyloxy, butenyloxy, propinyloxy, butinyloxy, methylthio, ethylthio, n- or i-propylthio, n-, i-, s- or t-butylthio, propenylthio, butenylthio, propinylthio, butinylthio, methylamino, ethylamino, n- or i-propylamino, n-, i-, s- or t-butylamino, propenylamino, butenylamino, propinylamino, butinylamino, dimethylamino or diethylamino, each of which is optionally substituted by fluorine, chlorine, cyano, methoxy, ethoxy, n- or i-propoxy, methylthio, ethylthio, n- or i-propylthio, or represents cyclopropyl, cyclobutyl, cyclobutyl, cyclopentyl, cyclohexyl, cyclopropyloxy, cyclobutyloxy, cyclopentyloxy, cyclohexyloxy, cyclo-propylmethyl, cyclobutylmethyl, cyclopentylmethyl or cyclohexylmethyl, each of which is optionally substituted by fluorine, chlorine, bromine, cyano, methyl, ethyl, n- or i-propyl, or represents phenyl, phenoxy, phenylthio, phenylamino or benzyl, each of which is optionally substituted by fluorine, chlorine, bromine, cyano, methyl, ethyl, n- or i-propyl, n-, i-, s- or t-butyl, methoxy or ethoxy, and $R^{12}$ represents methyl, ethyl, n- or i-propyl, n-, i-, s- or t-butyl, propenyl, butenyl, pentenyl, hexenyl, propinyl, butinyl, pentinyl or hexinyl, each of which is optionally substituted by fluorine, cyano, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, methylamino, ethylamino, n- or i-propylamino, n-, i-, s- or t-butylamino, dimethylamino, diethylamino, dipropylamino or dibutylamino, or represents cyclopropyl, cyclobutyl, cyclopentyl, cyclohexyl, cyclopropylmethyl, cyclobutylmethyl, cyclopentylmethyl, cyclohexylmethyl, cyclohexylethyl or cyclohexylpropyl, each of which is optionally substituted by fluorine, chlorine, bromine, cyano, methyl, ethyl, n- or i-propyl, or represents benzyl, phenylethyl, phenylpropyl, phenylbutyl, phenylethenyl, phenylpropenyl, phenylpropenyl, phenylbutenyl, phenylethinyl, phenylpropinyl or phenylbutinyl, each of which is optionally substituted by fluorine, chlorine, bromine, cyano, methyl, ethyl, n- or i-propyl, n-, i-, s- or t-butyl, methoxy or ethoxy, (c) alkylanilines comprising N-(l-ethyl-propyl)-3,4-dimethyl-2,6-dinitro-aniline(pendimethalin) or N,N-dipropyl-2,6-dinitro4-trifluoromethyl-aniline (trifluralin);

(d) carboxylic acids comprising 3,6-dichloro-pyridine-2-carboxylic acid (clopyralid), 2,4-dichloro-phenoxy acetic acid (2,4-D), 3,6-dichloro-2-methoxy-benzoic acid (dicamba), 4-amino-3,5-dichloro-6-fluoro-pyridin-2-yl-oxy-acetiacacid (fluroxypyr), ammonium 2-amino-4-(hydroxymethylphosphinyl)butanoate (glufosinate-ammonium), N-phosphonomethyl-glycine (glyphosate), 2-(4,5-dihydro-4-methyl-4-i-propyl-5-oxo-1H-imidazol-2-yl)-5-ethyl-pyridine-3-carboxylic acid (imazethapyr) or 2-(4,5-dihydro-4-methyl-4-i-propyl-5-oxo-1H-imidazol-2-yl)quinoline-3-carboxylic acid (imazaquin);

(e) carboxamides comprising N-(2-methoxy-1-methyl-ethyl)-N-(2-ethyl-6-methylphenyl)2-chloro-acetamide (metolachlor), N-ethoxymethyl-N-(2-ethyl-6-methylethyl)-2-chloroacetamide (acetochlor), N-methoxymethyl-N-(2,6-dimethylphenyl)-2-chloro-acetamide (alachlor), N-(2-methoxy -1-methylethyl)-N-(2,4-dimethyl-3-thienyl)-2-chloro-acetamide (dimethanamid), N-(1H-pyrazol-1-yl-methyl)-N-(2,6-dimethyl-phenyl)-2-chloro-acetamide (metazachlor) or N-i-propyl-N-phenyl-2-chloroacetamide (propachlor);

(f) diazin(on)es, or triazin(on)es comprising 2-chloro-4-ethylamino-6-i-propylamino-1,3,5-triazine (atrazine), 3-i-propyl-1H-2,1,3-benzothiadiazin4(3H)one 2,2-dioxide (bentazone), 2-chloro-4-ethylamino-6-(1-cyano-1-methyl-ethylamino)-1,3,5-triazine (cyanazine), 4-amino-6-t-butyl-4,5-dihydro-3-methylthio-1,2,4-triazin-5-one (metribuzin), O-(6-chloro-3-phenyl-4-pyridazinyl) S-octyl thiocarbonate (pyridate); 2-chloro4,6-bis-ethylamino-1,3,5-triazine (simazine) or 2-chloro-4-ethylamino-6-t-butylamino-1,3,5-triazine (terbuthylazine);

(g) ureas comprising N-(4,6-dimethoxy-pyrimidin-2-yl)-N'-(3-chloro-4-methoxycarbonyl-1-methyl-pyrazol-5-yl-sulphonyl)-urea (clopyrasulfurone), N-methoxy-N-methyl-N-[4-(3,4-dihydro-2-methoxy-2,4,4-trimethyl-2H-1-benzopyran 7-yl-oxy)-phenyl]-urea (metobenzuron), N-(4,6,-dimethoxy-pyrimidin-2-yl)-N'-(3-dimethylaminocarbonyl-pyridin-2-yl-sulphonyl)-urea (nicosulfuron), N-(4,6-bis-difluoromethoxy-pyrimidin-2-yl)-N'-(2-methoxycarbonyl-phenylsulphonyl)-urea (primisulfuron-methyl), N-(4-methoxy-6-methyl-1,3,5-triazin-2-yl)-N'-[2-(3,3,3-trifluoropropyl)-phenylsulphonyl]-urea (prosulfuron), N-(4,6-dimethoxypyrimidin-2-yl)-N'-(3-ethylsulphonyl-pyridin-2-yl-sulphonyl)-urea (rimsulfuron) or N-(4-methoxy-6-methyl-1,3,5-triazin-2-yl)-N'-(2-methoxycarbonyl-3-thienyl-sulphonyl)-urea (thifensulfuron-methyl);

(h) nitriles comprising 3,5-dibromo-4-hydroxy-benzonitrile (bromoxynil) or 3,5-diiod4-hydroxy-benzonitrile (ioxynil);

(i) thiocarbamates comprising S-ethyl N-di-i-butylthiocarbamate (butylate) or S-ethyl N-dipropylthiocarbamate (EPTC);

(j) active compounds from a variety of substance groups comprising N-2,6-difluoro-phenyl-5-methyl-[1,2,4]-triazolo-[1,5-a]-pyrimidine-2-sulphonamide (flumetsulam), 1,1'-dimethyl-4,4'-bipyridinium chloride (paraquat) or 2-(2-chloro-4-methyl-sulphonyl-benzoyl)-1,3-cyclohexanedione (sulcotrione).

3. Herbicidal compositions according to claim 1, wherein the active compound combination, the weight ratio of (1) aryluracil or arulthiouracil of formula (I) or of a compound of formula (Ia) which is isomeric thereto to a herbidical active compound from the second group of herbicides of the compound classes (a) to (j) is between 1:0.001 and 1:1000.

4. Method of controlling weeds, wherein the active compound combination according to claim 1 is allowed to act on weeds and/or their environment.

5. Method of controlling weeds according to claim 4, wherein the weeds are in maize crops.

6. Process for the preparation of herbicidal compositions wherein the active compound combination according to claim 1 is mixed with extenders and/or surfactants.

7. Process for the preparation of herbidical compositions according to claim 6, wherein the formulations comprise between 0.1 and 95% by weight of active compound.

8. Herbicidal compositions according to claim 1, wherein the active compound from the second group of herbicides is at least one (a) heteroaryloxyacetamides of the formula (II)

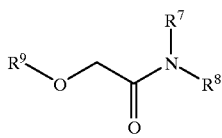

(II)

in which
- R⁷ represents methyl, ethyl, n- or i-propyl, n-, i- or s-butyl, propenyl, butenyl, propinyl, butinyl, methoxy, ethoxy, n- or i-propoxy, n-, i-, s- or t-butoxy, each of which is optionally substituted by fluorine, chlorine, cyano, methoxy or ethoxy,
- R⁸ represents methyl, ethyl, n- or i-propyl, n-, i-, s- or t-butyl, n-, i-, s- or t-pentyl, propenyl, butenyl, propinyl or butinyl, each of which is optionally substituted by fluorine, chlorine, cyano, methoxy or ethoxy, or represents phenyl which is optionally substituted by fluorine, chlorine, bromine, cyano, methyl, ethyl, trifluoromethyl, methoxy, ethoxy, difluoromethoxy or trifluoromethoxy, and
- R⁹ represents heteroaryl from the series consisting of 1,3-thiazol-2-yl, 1,2,4-thiadiazol-5-yl, 1,3,4-thiadiazol-2-yl, benzoxazol-2-yl, benzothiazol-2-yl, each of which is optionally substituted by fluorine, chlorine, bromine, cyano, methyl, ethyl, n- or i-propyl, n-, i-, s- or t-butyl, difluoromethyl, trifluoromethyl, dichloromethyl, trichloromethyl, methoxy, ethoxy, n- or i-propoxy, n-, i-, s- or t-butoxy, difluoromethoxy or trifluoromethoxy;

(b) carbamoyltriazolinones of the formula (III)

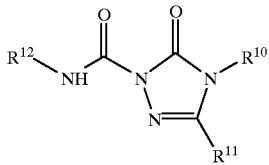

(III)

in which
- R¹⁰ represents hydrogen, hydroxyl, amino, or represents methyl, ethyl, n- or i-propyl, n-, i-, s- or t-butyl, propenyl, butenyl, propinyl or butinyl, methoxy, ethoxy, n- or i-propoxy, n-, i-, s- or t-butoxy, propenyloxy, butenyloxy, propinyloxy or butinyloxy, methylamino, ethylamino, n- or i-propylamino, n-, i-, s- or t-butylamino, propenylamino, butenylamino, propinylamino or butinylamino, ethylideneamino, propylideneamino, butylideneamino, dimethylamino or diethylamino, each of which is optionally substituted by fluorine, chlorine or cyano, or represents cyclopropyl, cyclobutyl, cyclopentyl, cyclohexyl, cyclopropylmethyl, cyclobutylmethyl, cyclopentylmethyl or cyclohexylmethyl, each of which is optionally substituted by fluorine, chlorine, bromine, cyano, methyl, ethyl, n- or i-propyl, or represents phenyl or benzyl, each of which is optionally substituted by fluorine, chlorine, bromine, cyano, methyl, ethyl, n- or i-propyl, n-, i-, s- or t-butyl, methoxy or ethoxy,
- R¹¹ represents methyl, ethyl, n- or i-propyl, n-, i-, s- or t-butyl, propenyl, butenyl, propinyl, butinyl, methoxy, ethoxy, n- or i-propoxy, n-, i-, s- or t-butoxy, propenyloxy, butenyloxy, propinyloxy, butinyloxy, methylthio, ethylthio, n- or i-propylthio, n-, i-, s- or t-butylthio, propenylthio, butenylthio, propinylthio, butinylthio, methylamino, ethylamino, n- or i-propylamino, n-, i-, s- or t-butylamino, propenylamino, butenylamino, propinylamino, butinylamino, dimethylamino or diethylamino, each of which is optionally substituted by fluorine, chlorine, cyano, methoxy, ethoxy, n- or i-propoxy, methylthio, ethylthio, n- or i-propylthio, or represents cyclopropyl, cyclobutyl, cyclobutyl, cyclopentyl, cyclohexyl, cyclopropyloxy, cyclobutyloxy, cyclopentyloxy, cyclohexyloxy, cyclo-propylmethyl, cyclobutylmethyl, cyclopentylmethyl or cyclohexylmethyl, each of which is optionally substituted by fluorine, chlorine, bromine, cyano, methyl, ethyl, n- or i-propyl, or represents phenyl, phenoxy, phenylthio, phenylamino or benzyl, each of which is optionally substituted by fluorine, chlorine, bromine, cyano, methyl, ethyl, n- or i-propyl, n-, i-, s- or t-butyl, methoxy or ethoxy, and
- R¹² represents methyl, ethyl, n- or i-propyl, n-, i-, s- or t-butyl, propenyl, butenyl, pentenyl, hexenyl, propinyl, butinyl, pentinyl or hexinyl, each of which is optionally substituted by fluorine, cyano, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, methylamino, ethylamino, n- or i-propylamino, n-, i-, s- or t-butylamino, dimethylamino, diethylamino, dipropylamino or dibutylamino, or represents cyclopropyl, cyclobutyl, cyclopentyl, cyclohexyl, cyclopropylmethyl, cyclobutylmethyl, cyclopentylmethyl, cyclohexylmethyl, cyclohexylethyl or cyclohexylpropyl, each of which is optionally substituted by fluorine, chlorine, bromine, cyano, methyl, ethyl, n- or i-propyl, or represents benzyl, phenylethyl, phenylpropyl, phenylbutyl, phenylethenyl, phenylpropenyl, phenylpropenyl, phenylbutenyl, phenylethinyl, phenylpropinyl or phenylbutinyl, each of which is optionally substituted by fluorine, chlorine, bromine, cyano, methyl, ethyl, n- or i-propyl, n-, i-, s- or t-butyl, methoxy or ethoxy, (c) alkylanilines comprising N-(1-ethyl-propyl)-3,4-dimethyl-2,6-dinitro-aniline(pendimethalin) or N,N-dipropyl-2,6-dinitro-4-trifluoromethyl-aniline (trifluralin);

(d) carboxylic acids comprising 3,6-dichloro-pyridine-2-carboxylic acid (clopyralid), 2,4-dichloro-phenoxy acetic acid (2,4-D), 3,6-dichloro-2-methoxy-benzoic acid (dicamba), 4-amino-3,5-dichloro-6-fluoro-pyridin-2-yl-oxy-acetiacacid (fluroxypyr), ammonium 2-amino4-(hydroxymethylphosphinyl)butanoate (glufosinate-ammonium), N-phosphonomethyl-glycine (glyphosate), (e) carboxamides comprising N-ethoxymethyl-N-2-ethyl-6-methyl-phenyl)-2-chloroacetamide (acetochlor), N-(2-methoxy-1-methyl-ethyl)-N-(2,4dimethyl-3-thienyl)-2-chloro-acetamide (dimethanamid), N-(1H-pyrazol-1-yl-methyl)-N-(2,6-ethyl-phenyl)-2-chloro-acetamide (metazachlor) or N-i-propyl-N-phenyl-2-chloro-acetamide (propachlor);

(f) diazin(on)es, or triazin(on)es comprising 2-chloro-4-ethylamino&i-propylamino-1,3,5-triazine (atrazine), 3-i-propyl-1H-2,1,3-benzothiadiazin4(3H)one 2,2-dioxide (bentazone), 2-chloro-4-ethylamino-6-(1-cyano-1-methyl-ethylamino)-1,3,5-triazine (cynanazine), O-(6-chloro-3-phenyl-4-pyridazinyl) S-octyl thiocarbonate (pyridate); 2-chloro4,6-bis-ethylamino-1,3,5-triazine (simazine) or 2-chloro-4-ethylamino-6-t-butylamino-1,3,5-triazine (terbuthylazine);

(g) ureas comprising —N-(4,6-dimethoxy-pyrimidin-2-yl)-N'-(3-chloro-4-methoxycarbonyl-1-methyl-pyrazol-5-yl-sulphonyl)-urea (clopyrasulfurone), N-methoxy-N-methyl-N-[4-(3,4-dihydro-2-methoxy-2,4,4-trimethyl-2H-1-benzopyran 7-yloxy)-phenyl]-urea (metobenzuron), N-4,6,-dimethoxy-pyrimidin- 2-yl)-N'-3dimethylaminocarbonyl-pyridin-2-yl-sulphonyl)-urea (nicosulfuron), N-(4,6-bis-difluoromethoxy-pyrimidin-2-yl)-N'-(2-methoxycarbonyl-phenylsulphonyl)-urea (primisulfuron-methyl), N-(4-methoxy-6-methyl-1,3,5-triazin-2-yl)-N'-[2-(3,3,3-trifluoropropyl)-phenylsulphonyl]-urea (prosulfuron), N-(4,6-dimethoxypyrimidin-2-yl)-N'-(3-ethylsulphonyl-pyridin-2-yl-sulphonyl)-urea (rimsulfuron) or N-(4-methoxy-6-methyl-1,3,5-triazin-2-yl)-N'-(2-methoxycarbonyl-3-thienyl-sulphonyl)-urea (thifensulfuron-methyl);

(h) nitrites comprising 3,5-dibromo-4-hydroxy-benzonitile (bromoxynil) or 3,5-diiod-4-hydroxy-benzonitrile (ioxynil);

(i) thiocarbamates comprising S-ethyl N-di-i-butylthiocarbamate (butylate) or S-ethyl N-dipropylthiocarbamate (EPTC);

(j) active compounds from a variety of substance groups comprising N-2,6-difluoro-phenyl-5-methyl-[1,2,4]-triazolo-[1,5-a]-pyrimidine-2-sulphonamide (flumetsulam), 1,1'-dimethyl4,4'-bipyridinium chloride (paraquat) or 2-(2-chloro-4-methyl-sulphonyl-benzoyl)-1,3-cyclohexanedione (sulcotrione).

* * * * *